(12) United States Patent
Samain et al.

(10) Patent No.: US 9,078,831 B2
(45) Date of Patent: Jul. 14, 2015

(54) COSMETIC TREATMENT METHOD USING A COMPOUND THAT CAN BE CONDENSED IN SITU AND A UV-RADIATION-FILTERING AGENT

(75) Inventors: Henri Samain, Bievres (FR); Guillaume Cassin, Villebon sur Yvette (FR); Didier Candau, Bievres (FR); Angelina Roudot, Paris (FR); Florence L'Alloret, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/516,389

(22) PCT Filed: Dec. 15, 2010

(86) PCT No.: PCT/FR2010/052744
§ 371 (c)(1),
(2), (4) Date: Aug. 21, 2012

(87) PCT Pub. No.: WO2011/073578
PCT Pub. Date: Jun. 23, 2011

(65) Prior Publication Data
US 2012/0328542 A1 Dec. 27, 2012

Related U.S. Application Data

(60) Provisional application No. 61/296,563, filed on Jan. 20, 2010, provisional application No. 61/296,561, filed on Jan. 20, 2010.

(30) Foreign Application Priority Data

Dec. 18, 2009  (FR) .................................... 09 59261
Dec. 18, 2009  (FR) .................................... 09 59262

(51) Int. Cl.
| | |
|---|---|
| *A61Q 17/04* | (2006.01) |
| *A61K 8/58* | (2006.01) |
| *A61K 8/33* | (2006.01) |
| *A61K 8/35* | (2006.01) |
| *A61K 8/49* | (2006.01) |
| *A61K 8/67* | (2006.01) |
| *A61K 8/86* | (2006.01) |
| *A61Q 19/00* | (2006.01) |

(52) U.S. Cl.
CPC . *A61K 8/585* (2013.01); *A61K 8/33* (2013.01); *A61K 8/35* (2013.01); *A61K 8/4933* (2013.01); *A61K 8/676* (2013.01); *A61K 8/86* (2013.01); *A61Q 19/00* (2013.01); *A61Q 19/002* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 2,950,986 A | 8/1960 | Bailey et al. | |
| 3,068,153 A | 12/1962 | Morehouse | |
| 5,686,065 A | 11/1997 | Haney | |
| 6,953,572 B1 * | 10/2005 | Samain et al. | 424/70.12 |
| 2006/0099159 A1 * | 5/2006 | Richard et al. | 424/59 |
| 2007/0183998 A1 * | 8/2007 | Suzuki et al. | 424/63 |
| 2009/0214455 A1 | 8/2009 | Blin et al. | |

FOREIGN PATENT DOCUMENTS

| | | |
|---|---|---|
| JP | H06-507385 A | 8/1994 |
| JP | 2009-520002 A | 5/2009 |
| WO | WO-9217184 A2 | 10/1992 |
| WO | WO-2007071706 A2 | 6/2007 |

OTHER PUBLICATIONS

Office Action issued Nov. 4, 2014 in Japanese Appln No. 2012-543878.

\* cited by examiner

*Primary Examiner* — Jyothsna Venkat
(74) *Attorney, Agent, or Firm* — Novak Druce Connolly Bove + Quigg LLP (57) ABSTRACT

The present invention relates to a method for the cosmetic treatment of the skin, comprising the application, to the skin:
- of a compound or group of compounds A capable of condensing in situ and exhibiting at least one reactive functional group $F_A$ which is free after condensation; and
- of a screening agent C which screens out UV radiation, comprising a reactive functional group $F_C$ capable of forming a covalent bond or a physical (ionic, hydrogen) bond by reaction with the functional group $F_A$.

13 Claims, 1 Drawing Sheet

COSMETIC TREATMENT METHOD USING A COMPOUND THAT CAN BE CONDENSED IN SITU AND A UV-RADIATION-FILTERING AGENT

CROSS REFERENCE TO RELATED APPLICATIONS

This application is a National Phase filing under 35 U.S.C. §371 of PCT/FR2010/052744 filed on Dec. 15, 2010; and this application claims priority to Application No. 0959261 filed in France on Dec. 18, 2009, and Application No. 0959262 filed in France on Dec. 18, 2009 under 35 U.S.C. §119; and this application claims the benefit of U.S. Provisional Application No. 61/296,563 filed on Jan. 20, 2010 and U.S. Provisional Application No. 61/296,561 filed on Jan. 20, 2010; the entire contents of all are hereby incorporated by reference.

The present invention relates to a method for the cosmetic treatment of the skin involving a compound, or group of compounds, capable of condensing in situ and an agent which screens out UV radiation.

Light radiation with a wavelength of between 280 and 400 nm makes possible browning of the human epidermis; rays with a wavelength of between 280 and 320 nm, known as UV-B rays, are responsible for red skin blotches which can harm the development of the tan. Rays with a wavelength of between 320 and 400 nm, known as UV-A rays, are capable of bringing about a detrimental change in the skin, with in particular a loss in elasticity and the appearance of wrinkles, resulting in premature ageing.

The UV rays thus have to be screened out and there currently exist protective cosmetic compositions for the human epidermis including organic UV screening agents which are active with regard to screening out UV-A and UV-B radiation.

It is known that a relatively high amount of UV screening agents has to be used to achieve a significant level of screening effectiveness against UV-A and UV-B radiation. However, these UV screening agents exhibit the following disadvantages when they are formulated at a high content: instability of the formulations and sensory failings. Moreover, photoprotective cosmetic compositions experience a decline in their screening effectiveness under the conditions of use of anti-sun products, due in particular to their low resistance to water.

It thus appears necessary to have available photoprotective cosmetic compositions with a good level of screening effectiveness obtained using limited contents of UV screening agents and exhibiting a good level of persistence towards water.

Surprisingly, the Applicant Company has shown that it is possible to have available photoprotective cosmetic compositions with a good level of screening effectiveness obtained using limited contents of UV screening agents and exhibiting a good level of persistence towards water. This is because the Applicant Company has discovered that it is possible to form, in the surface layers of the skin or on the skin, a condensate which confers, on the skin, a property of capturing UV screening agents. This "capturing" layer is formed by in situ condensation of at least one compound or group of compounds A, which will be described subsequently.

The advantageous properties obtained by virtue of the method according to the invention are in particular:

of promoting the homogeneous distribution of UV screening agents at the surface of the skin, of providing these UV screening agents with a sufficient point of attachment to remain in place on immersion in water and in particular water-soluble or water-dispersible screening agents.

In addition to the effects of reinforced resistance of the UV screening agents on the skin, the Applicant Company has discovered that the invention can lead to other advantages, such as an enhanced screening effectiveness.

This principle is made use of in the following way:

1—Application to the skin of a composition comprising an effective amount of a monomer A capable of reacting with itself. The monomer A thus has reactive functional groups to allow this reaction with itself to take place These functional groups are referred to as "intermonomer reaction functional groups". The monomer A is chosen in order for it also to have, after reaction, a reactive functional group referred to as "capturing functional group".

2—Reaction of this monomer A with itself (or with another monomer B) on the skin, for example by condensation, in particular when it is subjected to an increase in concentration obtained by evaporation of the solvent medium comprising it. This reaction results in the formation of a deposited layer on or in the skin. This deposited layer is not necessarily continuous but can be composed of a multitude of small connected domains.

3—Application of a screening agent to the condensate of the monomer A obtained on the skin. The screening agent can in particular react via the capturing functional group but also with one or more unreacted reactive groups referred to as "intermonomer reaction functional groups".

4—A chemical reaction occurs with formation of covalent bonds or physical (ionic or hydrogen) bonds between the screening agent and one or more capturing functional groups. This has the effect of modifying the condensate on the skin. It can in particular render it insoluble and thereby further increase its persistence on the skin (resistance to water, to sweat, to sebum, and the like), while maintaining, indeed even while reinforcing, the screening effectiveness of the UV screening agent or agents applied.

A subject-matter of the present invention is thus a method for the cosmetic treatment of the skin, comprising the application, to the skin:

of a compound or group of compounds A capable of condensing in situ and exhibiting at least one reactive functional group $F_A$ which is free after condensation; and of a screening agent C which screens out UV radiation, comprising a reactive functional group $F_C$ capable of forming a covalent bond or a physical (ionic, hydrogen) bond by reaction with the functional group $F_A$.

This is because the applicant company has been able to demonstrate that the application of these two types of compounds to the skin makes it possible to confer localized, rapid and long-lasting screening properties.

The capturing layer is formed in situ in the surface layers of the skin by condensation of a compound or of a group of compounds A.

Another subject-matter of the invention is the use of a compound or group of compounds A capable of condensing in situ and exhibiting at least one reactive functional group $F_A$ which is free after condensation, as agent for capturing, on the skin, an agent C which screens out UV radiation.

Another subject-matter of the invention is thus the use of a compound or group of compounds A capable of condensing in situ and exhibiting at least one reactive functional group $F_A$ which is free after condensation, for the capture, on the skin, of an agent C which screens out UV radiation, comprising a reactive functional group $F_C$ capable of forming a covalent or physical (ionic or hydrogen) bond by reaction with the functional group $F_A$.

According to a specific form of the invention, the material resulting from the condensation of A can be soluble in water, and the screening agent C can be chosen so that the reaction of the said agent C with the material resulting from the condensation of A results in a decrease in the solubility of the said material in water.

The invention thus relates to a method for the cosmetic treatment of the skin, comprising the application, to the skin:
- of a compound or group of compounds A capable of condensing in situ and exhibiting at least one reactive functional group $F_A$ which is free after condensation; and
- of a compound C of cosmetic interest, comprising a reactive functional group $F_c$ capable of forming a covalent bond or physical bond by reaction with the functional group $F_A$.
- the material resulting from the condensation of A being soluble in water, and C being chosen so that the reaction of the said compound C with the material resulting from the condensation of A results in a decrease in the solubility of the said material in water.

According to another aspect, the invention relates to a method for rendering a condensate insoluble in the skin, comprising the application, to the skin:
- of a compound or group of compounds A capable of condensing in situ and exhibiting at least one reactive functional group $F_A$ which is free after condensation; and
- of a screening agent C, comprising a reactive functional group $F_C$ capable of forming a covalent or physical bond by reaction with the functional group $F_A$, the material resulting from the condensation of A being soluble in water, and the screening agent C being chosen so that the reaction of the said compound C with the material resulting from the condensation of A results in a decrease in the solubility of the said material in water.

Another subject-matter of the invention is a method for reducing the solubility (indeed even rendering it insoluble), on or in the skin, of the material resulting from the condensation of a compound or group of compounds A capable of condensing in situ and exhibiting at least one reactive functional group $F_A$ which is free after condensation, the said material being soluble in water, comprising the application, to the said material, of a compound C of cosmetic interest comprising a reactive functional group $F_C$ capable of forming a chemical bond which can be covalent or physical, in particular ionic, by reaction with the functional group $F_A$, the screening agent C being chosen so that the reaction of the said agent C with the material resulting from the condensation of A results in a decrease in the solubility of the said material in water.

Another subject-matter of the invention is a method for obtaining, on the skin, an insoluble condensate exhibiting cosmetic properties, comprising the application, to the skin:
- of a compound or group of compounds A capable of condensing in situ and exhibiting at least one reactive functional group $F_A$ which is free after condensation; and
- of a screening agent C, comprising a reactive functional group $F_C$ capable of forming a covalent or physical bond by reaction with the functional group $F_A$,
- the material resulting from the condensation of A being soluble in water, and the screening agent C being chosen so that the reaction of the said screening agent C with the material resulting from the condensation of A results in a decrease in the solubility of the said material in water.

The invention also relates to the use of a screening agent C for reducing the solubility (indeed even rendering it insoluble) of a material resulting from the condensation of a compound or group of compounds A capable of condensing in situ and exhibiting at least one reactive functional group $F_A$ which is free after condensation, the said material being soluble in water, the screening agent C comprising a reactive functional group $F_C$ capable of forming a covalent or physical bond by reaction with the functional group $F_A$.

In the context of the present invention, the term "skin" describes the skin or scalp.

According to the invention, the term "agent which screens out UV radiation" is generally intended to denote any compound or any combination of compounds which, via mechanisms that are known per se for the absorption and/or reflection and/or scattering of UV-A and/or UV-B radiation, can prevent, or at least limit, the contact of the said radiation with a surface (skin, hair) onto which this or these compounds have been applied. In other words, these compounds may be UV-absorbing photoprotective organic screening agents or UV-scattering and/or UV-reflecting mineral pigments, and also mixtures thereof.

According to a first specific embodiment, a compound A capable of condensing in situ is used. In this embodiment, the compound A has to comprise at least two reactive functional groups: a functional group which makes it possible for the compound A to condense with itself and at least one "capturing" reactive functional group $F_A$ or one functional group which results in the formation of a functional group $F_A$ after condensation.

According to a second embodiment, a group of compounds A is used. This embodiment comprises the use of at least two molecules capable of condensing with one another. In this case, and according to the invention, the molecules constituting the group of compounds have to comprise a (several) functional group(s) making possible condensation of the group A and a (several) functional group(s) making possible the presence of a capturing reactive functional group $F_A$ after condensation.

According to a specific embodiment, the functional group(s) $F_A$ is present on only one of the compounds of the group of compounds A.

In another embodiment, the reactive functional group(s) is present on at least two compounds of the group of compounds.

In other words, with a group of compounds A composed of the molecules $A_1$ and $A_2$, $A_2$ may not comprise a capturing functional group. In this case, either the $A_1$ exhibits capturing functional groups or the latter appear on conclusion of the condensation reaction. Alternatively, the compound $A_2$ can comprise capturing functional groups. In this case, the compound $A_1$ cannot comprise any capturing functional group.

By way of illustration, the condensation of the group of compounds A can be represented in the following way.

Group of compounds A comprising two compounds: $A_1$ and $A_2$

1st case: $A_1$ comprises a capturing functional group (compound $F_A$-$A_1$); not $A_2$ condensation product:

2nd case: $A_1$ and $A_2$ comprise a capturing functional group (identical or different) (compound $F_A$-$A_1$ and compound $F_A$-$A_1$) condensation product:

It is understood that this particularly simplified schematic example is presented only by way of illustration and should not be regarded as limiting the invention.

According to a preferred embodiment, the process according to the invention comprises:
- the application to the skin of a compound A capable of condensing in situ and exhibiting at least one reactive functional group $F_A$ which is free after condensation; and
- the application of an agent C which screens out UV radiation, comprising a reactive functional group $F_C$ capable of forming a covalent bond or a physical (ionic, hydrogen) bond by reaction with the functional group $F_A$.

The condensation and capturing functional groups will be described subsequently with reference to A, which will denote without distinction a compound A or a group of compounds A (for example $A_1+A_2$) described above.

The capturing functional group or groups have to be at least in part free after condensation of A in order to be able to react with the screening agent C. Alternatively, the capturing functional group or groups may not exist or may not be in the free form in the compound or group of compounds A but appear or become free on conclusion of the condensation thereof. They may, for example, be primary amine functional groups which might appear subsequent to the action of enzyme naturally present on the skin.

Preferably, the capturing functional groups which are free after condensation have to be present in a proportion such that $F_{capt}/A > 0.1$ and preferably $> 0.5$, $F_{capt}$ and A respectively representing the amounts by number of capturing functional groups which are free after condensation and of molecules of A. In other words, there exists, after condensation, at least one free capturing functional group per 10 molecules of A, preferably at least 5 free capturing functional groups.

The capturing functional groups $F_A$ of the compound or group of compounds A are typically chosen from amines and other nucleophilic functional groups, such as hydroxyl, thiol, sulphate and phosphate functional groups. Preferably, they are amines; preferably, primary amines.

The condensation of A can originate from the reaction of a nucleophilic entity with an electrophilic entity. According to a first alternative, the condensation functional groups are typically those which make possible the creation of a bond by elimination of a water molecule, according to the following equation:

In a specific embodiment, the compounds employed are organosilanes.

According to a second alternative, the condensation can originate from the reaction of an entity by pulling a proton off a second entity, in particular according to one of the following equations:

and

In the above equations, R and R' denote, independently of one another, any group of atoms, it being understood that the product of the condensation of A has to comprise at least one free functional group $F_A$.

Preferably, the condensation takes place according to the first alternative described above.

In a specific embodiment, the compound A is an organic silicon compound comprising from 1 to 3 silicon atoms and at least two hydroxyl or hydrolysable groups per molecule. The compound A is thus chosen from organosilanes comprising a silicon atom and organosiloxanes comprising two or three silicon atoms, preferably two silicon atoms.

According to a preferred embodiment, the compound A is an organosilane. The compound A can in particular be an alkoxysilane and preferably a functionalized alkoxysilane.

The group of compounds A can be the mixture of an organic silicon compound as described above (compound $A_1$) and of at least one other compound (compound $A_2$) such that the group comprising the organic silicon compound and the compound $A_2$ is capable of condensing in situ.

Preferably, the compound A (or at least one of the molecules of the group of compounds A) corresponds to the formula:

in which:
$R_4$ represents a halogen or an OR' or $R'_1$ group;
$R_5$ represents a halogen or an OR' or $R'_2$ group;
$R_6$ represents a halogen or an OR''' or $R'_3$ group;
and $R_1$, $R_2$, $R_3$, R', R'', R''', $R'_1$, $R'_2$ and $R'_3$ represent, independently of one another, a linear or branched and saturated or unsaturated hydrocarbon group optionally carrying additional chemical groups, such as acid or amine groups, it being possible in addition for $R_1$, $R_2$, R', R'' and R''' to denote hydrogen, and
at least two of the groups $R_4$, $R_5$ and $R_6$ being different from the groups $R'_1$, $R'_2$ and $R'_3$.

Preferably, $R_1$, $R_2$, R', R'' and R''', $R'_1$, $R'_2$ and $R'_3$ represent a $C_1$ to $C_{12}$ alkyl group, a $C_6$ to $C_{14}$ aryl group, a $C_1$ to $C_8$ alkyl-$C_6$ to $C_{14}$ aryl group, and a $C_6$ to $C_{14}$ aryl-$C_1$ to $C_8$ alkyl group; and $R_3$ is preferably a $C_1$ to $C_{12}$ alkyl, $C_6$ to $C_{14}$ aryl, $C_1$ to $C_8$ alkyl-$C_6$ to $C_{14}$ aryl and $C_6$ to $C_{14}$ aryl-$C_1$ to $C_8$ alkyl group.

The preferred organosiloxanes in the compositions of the present invention can be represented by the formula:

in which:
$R_1$, $R_2$, $R_3$, $R_5$ and $R_6$ are defined as above;
$R'_4$ represents a halogen (fluorine, bromine, chlorine or iodine) or an $OR_{11}$ group;
$R_7$ represents a halogen or a group $OR_{10}$ or $R''_1$,
$R_9$ represents a halogen or an $OR_8$, $R''_2$ or $R_3NR_1R_2$ group;

R"$_1$, R"$_2$, R$_8$, R$_{10}$ and R$_{11}$ represent a linear or branched and saturated or unsaturated hydrocarbon group optionally carrying additional chemical groups, such as basic solubilizing groups;

it being possible for R$_{11}$, R$_{10}$ and R$_8$ to additionally denote hydrogen.

Preferably, R"$_1$, R"$_2$, R$_8$ or R$_{10}$ and R$_{11}$ represent a C$_1$ to C$_{12}$ alkyl group, a C$_6$ to C$_{14}$ aryl group, a C$_1$ to C$_8$ alkyl-C$_6$ to C$_{14}$ aryl group and a C$_6$ to C$_{14}$ aryl-C$_1$ to C$_8$ alkyl group.

At least one of the groups R$_6$, R$_7$ and R$_9$ denotes a halogen or an OR''', OR$_{10}$ or OR$_8$ group.

Preferably, the halogen is chlorine.

A particularly preferred class of organic silicon compounds is composed of the compounds of formula:

in which the R radicals, which are identical or different, are chosen from C$_1$-C$_6$ alkyl radicals, such as methyl, ethyl, propyl and butyl, and n is an integer from 1 to 6 and preferably from 2 to 4.

In particular, the compound A is an alkoxysilane comprising at least one nucleophilic capturing functional group, in particular γ-aminopropyltriethoxysilane, known as APTES in the continuation of this text, or one of its derivatives.

The compound A$_2$ capable of being involved in the method according to the present invention, when a group of compounds A is applied to the skin, can, for example, correspond to the same definition as the compound A given above. The compound A$_2$ can in particular be chosen from the molecules having the ability to form an Si—O—Si bond. By way of illustration, mention may be made of methyltriethoxysilane (MTES).

A is chosen so that the condensation only takes place once it has reached the region where this condensation has to take place. For example, the compound A may be highly reactive, and the condensation thereof may take place at the surface of the skin. Alternatively, the condensation may take place once the compound A has penetrated more or less deeply into the skin.

Mention may in particular be made, as chemical functional groups F$_C$ capable of reacting with at least one of the free capturing functional groups of the material resulting from the condensation of the compound A or of the group of compounds A, of carbonyl, carboxylic acid, sulphonic acid, ester, amine and hydroxyl functional groups.

According to a particularly preferred form of the invention, in order to reinforce the resistance of the capturing material formed on the skin (resistance to rubbing actions, to water, to sweat, to sebum, and the like), use will be made, in the method of the invention, of a mixture of compound A$_1$ and A$_2$ as defined above, in particular a mixture composed of γ-aminopropyltriethoxysilane (APTES) and methyltriethoxysilane (MTES). The ratios by weight of A$_1$ to A$_2$ will preferably vary from 10/90 to 90/10 and more preferably from 30/70 to 70/30.

Screening Agents

The screening agents in accordance with the invention are chosen from organic UV screening agents, inorganic screening agents or their mixtures.

The organic UV screening agents are chosen especially from cinnamic derivatives; anthranilates; salicylic derivatives; dibenzoylmethane derivatives, camphor derivatives; hydroxyphenyl benzophenone derivatives; β,β-diphenylacrylate derivatives; triazine derivatives; benzotriazole derivatives; benzalmalonate derivatives, especially those mentioned in U.S. Pat. No. 5,624,663; benzimidazole derivatives; imidazolines; bis-benzazolyl derivatives as described in patents EP 669 323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB 2 303 549, DE 197 26 184 and EP 893 119; benzoxazole derivatives as described in patent applications EP 0 832 642, EP 1 027 883, EP 1 300 137 and DE 101 62 844; screening polymers and screening silicones such as those described especially in patent application WO 93/04665; α-alkylstyrene-based dimers, such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 133 981; merocyanin derivatives such as those described in patent applications WO 04/006 878, WO 05/058 269 and WO 06/032 741; and mixtures thereof.

As examples of additional organic photoprotective agents, mention may be made of those denoted hereinbelow under their INCI name:

Cinnamic Derivatives:
  Ethylhexyl Methoxycinnamate sold especially under the trade name Parsol MCX by DSM Nutritional Products,
  Isopropyl Methoxycinnamate,
  Isoamyl Methoxycinnamate sold under the trade name Neo Heliopan E 1000 by Symrise,
  DEA-Methoxycinnamate,
  Diisopropyl Methyl Cinnamate,
  Glyceryl Ethylhexanoate Dimethoxycinnamate.
Dibenzoylmethane Derivatives:
  Butyl Methoxydibenzoylmethane sold especially under the trade name Parsol 1789 by DSM,
  Isopropyl Dibenzoylmethane.
para-Aminobenzoic Acid Derivatives:
  PABA,
  Ethyl PABA,
  Ethyl Dihydroxypropyl PABA,
  Ethylhexyl Dimethyl PABA sold in particular under the name Escalol 507 by ISP,
  Glyceryl PABA,
  PEG-25 PABA sold under the name Uvinul P25 by BASF.
Salicylic Derivatives:
  Homosalate sold under the name Eusolex HMS by Rona/EM Industries,
  Ethylhexyl Salicylate sold under the name Neo Heliopan OS by Symrise,
  Dipropylene Glycol Salicylate sold under the name Dipsal by Scher,
  TEA Salicylate sold under the name Neo Heliopan TS by Symrise.
β,β-Diphenylacrylate Derivatives:
  Octocrylene sold especially under the trade name Uvinul N539 by BASF,
  Etocrylene sold in particular under the trade name Uvinul N35 by BASF.
Hydroxyphenyl Benzophenone Derivatives:
  Benzophenone-1 sold under the trade name Uvinul 400 by BASF,
  Benzophenone-2 sold under the trade name Uvinul D50 by BASF,
  Benzophenone-3 or oxybenzone sold under the trade name Uvinul M40 by BASF,
  Benzophenone-4 sold under the trade name Uvinul MS40 by BASF, Benzophenone-5, Benzophenone-6 sold under the trade name Helisorb 11 by Norquay, Benzophenone-8 sold under the trade name Spectra-Sorb UV-24 by American Cyanamid, Benzophenone-9 sold under the trade name Uvinul DS-49 by BASF, Benzophenone-12, n-hexyl 2-(4-diethylamino-2-hydroxybenzoyl)benzoate sold under the trade name Uvinul A+, or in the form of a mixture with octyl methoxycinnamate under the trade name Uvinul A+B by the company BASF.

Benzylidene Camphor Derivatives:

3-Benzylidene Camphor manufactured under the name Mexoryl SD by Chimex,

4-Methylbenzylidene Camphor sold under the name Eusolex 6300 by Merck,

Benzylidene Camphor Sulfonic Acid manufactured under the name Mexoryl SL by Chimex, Camphor Benzalkonium Methosulfate manufactured under the name Mexoryl SO by Chimex, Terephthalylidene Dicamphor Sulfonic Acid manufactured under the name Mexoryl SX by Chimex, Polyacrylamidomethyl Benzylidene Camphor manufactured under the name Mexoryl SW by Chimex.

Phenylbenzimidazole Derivatives:

Phenylbenzimidazole Sulfonic Acid sold in particular under the trade name Eusolex 232 by Merck, Disodium Phenyl Dibenzimidazole Tetrasulfonate sold under the trade name Neo Heliopan AP by Symrise.

Phenylbenzotriazole Derivatives:

Drometrizole Trisiloxane sold under the name Silatrizole by Rhodia Chimie,

Methylene Bis-Benzotriazolyl Tetramethylbutylphenol sold in solid form under the trade name Mixxim BB/100 by Fairmount Chemical, or in micronized form as an aqueous dispersion under the trade name Tinosorb M by Ciba Specialty Chemicals.

Triazine Derivatives:

Bis-Ethylhexyloxyphenol Methoxyphenyl Triazine sold under the trade name Tinosorb S by Ciba Geigy, Ethylhexyl Triazone sold in particular under the trade name Uvinul T150 by BASF, Diethylhexyl Butamido Triazone sold under the trade name Uvasorb HEB by Sigma 3V, 2,4-Bis(n-butyl 4'-aminobenzalmalonate)-6-[(3-{1,3,3,3-tetramethyl-1-[(trimethylsilyl)oxy]disiloxanyl}propyl)amino]-s-triazine, 2,4,6-Tris(diisobutyl 4'-aminobenzalmalonate)-s-triazine, 2,4,6-Tris(dineopentyl 4'-aminobenzalmalonate)-s-triazine, 2,4-Bis(dineopentyl 4'-aminobenzalmalonate)-6-(n-butyl 4'-aminobenzoate)-s-triazine, the symmetrical triazine screening agents described in U.S. Pat. No. 6,225,467, patent application WO 2004/085412 (see compounds 6 and 9) or the document "Symmetrical Triazine Derivatives" IP.COM Journal, IP.COM INC West Henrietta, N.Y., US (20 Sep. 2004), especially 2,4,6-tris(biphenyl)-1,3,5-triazines (in particular 2,4,6-tris(biphenyl-4-yl-1,3,5-triazine) and 2,4,6-tris(terphenyl)-1,3,5-triazine which is also mentioned in Beiersdorf patent applications WO 06/035000, WO 06/034982, WO 06/034991, WO 06/035007, WO 2006/034992 and WO 2006/034985.

Anthranilic Derivatives:

Menthyl Anthranilate sold under the trade name Neo Heliopan MA by Symrise.

Imidazoline Derivatives:

Ethylhexyl Dimethoxybenzylidene Dioxoimidazoline Propionate.

Benzalmalonate Derivatives:

Polyorganosiloxane containing benzalmalonate functional groups, for instance Polysilicone-15, sold under the trade name Parsol SLX by DSM Nutritional Products.

4,4-Diarylbutadiene derivatives:

-1,1-dicarboxy(2,2'-dimethylpropyl)-4,4-diphenylbutadiene.

Benzoxazole Derivatives:

2,4-Bis[4-[5-(1,1-dimethylpropyl)benzoxazol-2-yl]phenylimino]-6-[(2-ethylhexyl)imino]-1,3,5-triazine, sold under the name of Uvasorb K2A by Sigma 3V, and mixtures thereof.

The preferential organic screening agents are chosen from:
Ethylhexyl Methoxycinnamate,
Ethylhexyl Salicylate,
Homosalate,
Butyl Methoxydibenzoylmethane,
Octocrylene,
Phenylbenzimidazole Sulfonic Acid,
Benzophenone-3,
Benzophenone-4,
Benzophenone-5,
n-Hexyl 2-(4-diethylamino-2-hydroxybenzoyl)benzoate,
4-Methylbenzylidene Camphor,
Terephthalylidene Dicamphor Sulfonic Acid,
Disodium Phenyl Dibenzimidazole Tetrasulfonate,
Methylene Bis-Benzotriazolyl Tetramethylbutylphenol,
Bis-Ethylhexyloxyphenyl Methoxyphenyl Triazine
Ethylhexyl Triazone,
Diethylhexyl Butamido Triazone,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
2,4,6-Tris(biphenyl-4-yl)-1,3,5-triazine,
2,4,6-Tris(terphenyl)-1,3,57-triazine,
Drometrizole Trisiloxane
Polysilicone-15,
1,1-Dicarboxy(2,2'-dimethylpropyl)-4,4-diphenylbutadiene.
2,4-Bis[4-[5-(1,1-dimethylpropyl)benzoxazol-2-yl]phenylimino]-6-[(2-ethylhexyl)imino]-1,3,5-triazine,
and mixtures thereof.

The mineral UV screening agents used in accordance with the present invention are metal oxide pigments. More preferentially, the mineral UV screening agents of the invention are metal oxide pigments with a mean elemental particle size of less than or equal to 500 nm, more preferentially between 5 nm and 500 nm and even more preferentially between 10 nm and 100 nm, and preferentially between 15 and 50 nm.

They may be chosen especially from titanium oxide, zinc oxide, iron oxide, zirconium oxide and cerium oxide, or mixtures thereof.

Such coated or uncoated metal oxide pigments are described in particular in patent application EP-A-0 518 773. Commercial pigments that may be mentioned include the products sold by the companies Kemira, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium) of polyethylene, silicones, proteins (collagen, elastin), alkanolamines, silicon oxides, metal oxides or sodium hexametaphosphate.

The coated pigments are more particularly titanium oxides that have been coated:
- with silica, such as the product Sunveil from the company Ikeda,
- with silica and iron oxide, such as the product Sunveil F from the company Ikeda,
- with silica and alumina, such as the products Microtitanium Dioxide MT 500 SA and Microtitanium Dioxide MT 100 SA from the company Tayca and Tioveil from the company Tioxide,
- with alumina, such as the products Tipaque TTO-55 (B) and Tipaque TTO-55 (A) from the company Ishihara and UVT 14/4 from the company Kemira,
- with alumina and aluminium stearate, such as the products Microtitanium Dioxide MT 100 T, MT 100 TX, MT 100 Z and MT-01 from the company Tayca, the products Solaveil CT-10 W and Solaveil CT 100 from the company Uniqema and the product Eusolex T-AVO from the company Merck,
- with silica, alumina and alginic acid, such as the product MT-100 AQ from the company Tayca,
- with alumina and aluminium laurate, such as the product Microtitanium Dioxide MT 100 S from the company Tayca,
- with iron oxide and iron stearate, such as the product Microtitanium Dioxide MT 100 F from the company Tayca,
- with zinc oxide and zinc stearate, such as the product BR351 from the company Tayca,
- with silica and alumina and treated with a silicone, such as the products Microtitanium Dioxide MT 600 SAS, Microtitanium Dioxide MT 500 SAS or Microtitanium Dioxide MT 100 SAS from the company Tayca,
- with silica, alumina and aluminium stearate and treated with a silicone, such as the product STT-30-DS from the company Titan Kogyo,
- with silica and treated with a silicone, such as the product UV-Titan X 195 from the company Kemira,
- with alumina and treated with a silicone, such as the products Tipaque TTO-55 (S) from the company Ishihara or UV Titan M 262 from the company Kemira,
- with triethanolamine, such as the product STT-65-S from the company Titan Kogyo,
- with stearic acid, such as the product Tipaque TTO-55 (C) from the company Ishihara,
- with sodium hexametaphosphate, such as the product Microtitanium Dioxide MT 150 W from the company Tayca.

$TiO_2$ treated with octyltrimethylsilane, sold under the trade name T 805 by the company Degussa Silices, $TiO_2$ treated with a polydimethylsiloxane, sold under the trade name 70250 Cardre UF TiO2SI3 by the company Cardre, anatase/rutile $TiO_2$ treated with a polydimethylhydrogenosiloxane, sold under the trade name Microtitanium Dioxide USP Grade Hydrophobic by the company Color Techniques.

The uncoated titanium oxide pigments are sold, for example, by the company Tayca under the trade names Microtitanium Dioxide MT 500 B or Microtitanium Dioxide MT 600 B, by the company Degussa under the name P 25, by the company Wackherr under the name Transparent titanium oxide PW, by the company Miyoshi Kasei under the name UFTR, by the company Tomen under the name ITS and by the company Tioxide under the name Tioveil AQ.

The uncoated zinc oxide pigments are, for example:
- those sold under the name Z-Cote by the company Sunsmart;
- those sold under the name Nanox by the company Elementis;
- those sold under the name Nanogard WCD 2025 by the company Nanophase Technologies.

The coated zinc oxide pigments are, for example:
- those sold under the name Zinc Oxide CS-5 by the company Toshibi (ZnO coated with polymethylhydrogenosiloxane);
- those sold under the name Nanogard Zinc Oxide FN by the company Nanophase Technologies (as a 40% dispersion in Finsolv TN, C12-C15 alkyl benzoate);
- those sold under the name "Daitopersion ZN-30" and "Daitopersion ZN-50" by the company Daito (dispersions in cyclopolymethylsiloxane/oxyethylenated polydimethylsiloxane, containing 30% or 50% of nanozinc oxides coated with silica and polymethylhydrogenosiloxane);
- those sold under the name "NFD Ultrafine ZNO" by the company Daikin (ZnO coated with perfluoroalkyl phosphate and copolymer based on perfluoroalkylethyl as a dispersion in cyclopentasiloxane);
- those sold under the name SPD-Z1 by the company Shin-Etsu (ZnO coated with silicone-grafted acrylic polymer, dispersed in cyclodimethylsiloxane);
- those sold under the name Escalol Z100 by the company ISP (alumina-treated ZnO dispersed in an ethylhexyl methoxycinnamate/PVP-hexadecene/methicone copolymer mixture);
- those sold under the name Fuji ZnO-SMS-10 by the company Fuji Pigment (ZnO coated with silica and polymethylsilsesquioxane);
- those sold under the name Nanox Gel TN by the company Elementis (ZnO dispersed at a concentration of 55% in C12-C15 alkyl benzoate with hydroxystearic acid polycondensate).

The uncoated cerium oxide pigments are sold under the name Colloidal Cerium Oxide by the company Rhône-Poulenc.

The uncoated iron oxide pigments are sold, for example, by the company Arnaud under the names Nanogard WCD 2002 (FE 45B), Nanogard Iron FE 45 BL AQ, Nanogard FE 45R AQ and Nanogard WCD 2006 (FE 45R) or by the company Mitsubishi under the name TY-220.

The coated iron oxide pigments are sold, for example, by the company Arnaud under the names Nanogard WCD 2008 (FE 45B FN), Nanogard WCD 2009 (FE 45B 556), Nanogard FE 45 BL 345 and Nanogard FE 45 BL or by the company BASF under the name Transparent Iron Oxide.

Mention may also be made of mixtures of metal oxides, especially of titanium dioxide and of cerium dioxide, including the silica-coated equal-weight mixture of titanium dioxide and of cerium dioxide, sold by the company Ikeda under the name Sunveil A, and also the alumina, silica and silicone-coated mixture of titanium dioxide and of zinc dioxide, such as the product M 261 sold by the company Kemira, or the alumina-, silica- and glycerol-coated mixture of titanium dioxide and of zinc dioxide, such as the product M 211 sold by the company Kemira.

According to the invention, coated or uncoated titanium oxide pigments are particularly preferred.

In a preferred form of the invention, the screening agents are water-soluble or water-dispersible and are generally chosen from organic screening agents exhibiting one or more anionic, preferably sulphonate or carboxylate, functional groups.

In the continuation of the present description, "water-soluble or water-dispersible UV screening agent" is understood to mean any agent which screens out UV radiation which is capable of being completely dissolved in the molecular state in the aqueous phase of the composition or else of being dissolved in the colloidal form (for example in the micelle form) in the aqueous phase of the composition.

The UV screening agents envisaged preferably comprise chromophores, such as 4-aminobenzoic acid (PABA), ferulic acid, cinnamic acid, salicylic acid, benzimidazole, benzylidenecamphor or benzophenone.

Mention may be made, for example, of:
PABA,
Glyceryl PABA,
PEG-25 PABA
TEA Salicylate
DEA-Methoxycinnamate,
Benzophenone-4, sold under the trade name "Uvinul MS40" by BASF,
Benzophenone-5,
Benzophenone-12,
Phenylbenzimidazolesulfonic acid,
Benzylidene Camphor Sulfonic Acid
Camphor Benzalkonium Methosulfate,
Terephthalylidene Dicamphor Sulfonic Acid,
Disodium Phenyl Dibenzimidazole Tetrasulfonate.
Use will more preferably be made of
Phenylbenzimidazolesulfonic acid,
Terephthalylidene Dicamphor Sulfonic Acid,
Disodium Phenyl Dibenzimidazole Tetrasulfonate or their mixtures.

According to a preferred embodiment, the method according to the invention comprises:
the application to the skin of a compound A capable of condensing in situ and exhibiting at least one reactive functional group $F_A$ which is free after condensation; and
the application of a water-soluble or water-dispersible UV screening agent comprising a reactive functional group $F_C$ capable of forming an ionic (in particular carboxylate or sulphonate) bond by reaction with the functional group $F_A$.

The screening agent(s) is (are) generally present in proportions ranging from 0.1% to 15% by weight, preferably from 0.2% to 10% by weight and more preferentially from 1% to 6% by weight, with respect to the total weight of the composition.

The compound A (or the group of compounds A) and the screening agent C are chosen as a function of the property (properties) which it is desired to confer on the skin.

The method according to the invention comprises the application to the skin of a compound or group of compounds A capable of condensing, in particular when it is subjected to an increase in concentration obtained by evaporation of the medium in which it is present. The compound or group of compounds A thus comprises reactive functional groups for making this condensation possible, as has been mentioned above.

This condensation results in the formation of a deposited layer on the skin. This deposited layer is not necessarily continuous but can be composed of a multitude of connected domains. The compound A is chosen in order for the material resulting from the condensation thereof to exhibit free reactive functional groups referred to as "capturing functional groups".

The screening agent C is also applied to the skin.

The screening agent C can react with the product of the condensation of A, via the capturing functional group $F_A$ which is free after condensation and a functional group $F_C$ present on the screening agent C.

The method according to the invention comprises the sequential application of the screening agent C.

In one embodiment of the invention, in a first step, the compound A (or the group of compounds A) is applied to a region of the skin. Subsequently, after a more or less lengthy time which can be between 1 minute and 5 hours, preferably from 1 minute to 1 hour, more preferably still between 2 and 10 minutes, the screening agent C is applied to the same region of the skin.

In the context of this embodiment, the condensation of the compound A (or of the group of compounds A) can take place spontaneously, or may have been triggered, before the application of the screening agent C. The screening agent C can then react with the condensate via the free capturing functional group or groups on the condensate. The screening agent C can also react with one or more reactive functional groups other than the capturing functional groups, in particular with reactive functional groups which might have been able to participate in the reaction of A with itself but have not reacted.

Thus, in the specific case where the compound A is an organosilane carrying a capturing functional group, it is understood that the screening agent C can react with the capturing functional group and with uncondensed silanols of the condensate.

A chemical reaction then occurs, with formation of covalent or physical bonds between the screening agent C and one or more reactive functional groups, more particularly with the capturing functional groups $F_A$ present on the condensate of the compound A or of the group of compounds A. This can have the effect of modifying the material on the skin. This reaction can in particular render the condensate insoluble and can thus further increase its persistence on and/or in the skin (resistance to water, to sweat, to sebum, and the like), while maintaining, indeed even while reinforcing, the screening properties conferred by the screening agent C.

The invention can be employed with the use of methods which accelerate or inhibit the reactions carried out in the invention, for example heat or cold, microwaves, pH agents or catalysts.

It is also possible to act from the surface of the skin on the reaction between the screening agent C and the compound or group of compounds A, for example in order to control it or to make it faster.

According to an alternative form of the method according to the invention, first the compound A is applied and then there is a wait for the reaction for the condensation of A to take place. This can be fast or slow, involve or not involve drying the skin, or involve or not involve an activation with, for example, use of a source of heat or another source of energy. At this stage, it is possible to apply the screening agent C, or to rinse and then apply the screening agent C. The screening agent C can be left to react with the material resulting from the condensation of A. It is also possible to activate the reaction between A and C. After reaction between A and C, rinsing may or may not be carried out.

According to a specific embodiment, the compound A is applied in a form or under conditions which do not make possible the condensation reaction. There is a wait for the compound A to penetrate. The reaction is then triggered, either by adding an adjuvant (for example a pH agent) or by changing the conditions, for example by changing the temperature (in particular by increasing it). Once the condensation has begun, and optionally after a rinsing stage, the screening agent C is applied, as above.

In another alternative form, the compound A or the group of compounds A is applied and then the screening agent C is applied under conditions where the capturing reaction cannot take place. Condensation takes place. Once condensation has begun, the reaction of the screening agent C with the condensate of A is triggered.

In a specific embodiment, the compounds A and C are mixed before application to the skin (extemporaneous mixing). This mixing can be carried out before application or during the application to the skin (mixing directly on the region of the skin to be treated).

The compound A (or the group of compounds A) and the screening agent C can thus be applied concomitantly. In this case,
- the compounds A and screening agent C are chosen in order for the presence of C not to prevent the condensation of A; or
- the compounds A and screening agent C and/or the conditions of use are chosen so that the condensation of A is faster than the reaction of C; or
- the compound A can condense while the screening agent C cannot react. After a certain time, the reaction of the screening agent C is triggered by a subsequent action or automatically, for example by change in pH or in temperature or by application of a light source.

In a specific embodiment, the result of the condensation of A is applied to the skin. For example, a polyAPTES film can be applied. The screening agent C is subsequently applied.

In another embodiment, first the screening agent C is applied and then the compound A is applied.

Generally, the reactions can be accelerated by the use of suitable catalysts, for example pH agents, salts, metals and/or enzymes.

Another subject-matter of the present invention is the joint use of a cosmetic composition comprising an effective amount of a compound A capable of condensing in situ on the skin and of a cosmetic composition comprising an effective amount of a screening agent C which will react with one or more free reactive functional groups of the material resulting from the condensation of the compound A.

Formulation Forms

The compound A, or the group of compounds A, and the screening agent C can be formulated in compositions comprising a physiologically acceptable medium.

These compositions can be provided according to any formulation form conventionally used in the application envisaged. Needless to say, a person skilled in the art will take care to select the components and optional additional ingredients and/or active agents, and/or the amount thereof, such that the advantageous properties of the compound A (or of the group of compounds A) and of the screening agent C are not, or are not substantially, adversely affected by the envisaged addition.

In a specific embodiment, the compositions used according to the invention are aqueous compositions.

The compositions comprising the screening agent C employed for the photoprotection of the skin can be prepared according to techniques well known to a person skilled in the art. It should be noted that the formulation forms and active agents described below can be used for the formulation of the compound A.

The compositions employed according to the invention may comprise standard cosmetic adjuvants chosen especially from fatty substances, organic solvents, ionic or nonionic and hydrophilic or lipophilic thickeners, softeners, humectants, opacifiers, stabilizers, emollients, silicones, antifoams, fragrances, preserving agents, anionic, cationic, nonionic, zwitterionic or amphoteric surfactants, active agents, fillers, polymers, propellants, acidifying or basifying agents or any other ingredient usually used in cosmetics and/or dermatology. These cosmetic adjuvants can be incorporated without distinction in the composition comprising A, in the composition comprising the screening agent C, or in both compositions.

The fatty substances may consist of an oil or a wax other than the nonpolar waxes as defined above, or mixtures thereof. The term oil means a compound that is liquid at room temperature. The term wax means a compound that is solid or substantially solid at room temperature and whose melting point is generally greater than 35° C.

Oils that may be mentioned include mineral oils (paraffin); vegetable oils (sweet almond oil, macadamia oil, blackcurrant oil or jojoba oil); synthetic oils, for instance perhydrosqualene, fatty alcohols, fatty amides (for instance isopropyl lauroyl sarcosinate sold under the name Eldew SL-205 by the company Ajinomoto), fatty acids or fatty esters, for instance the C12-C15 alkyl benzoate sold under the trade name Finsolv TN or Witconol TN by the company Witco, 2-ethylphenyl benzoate, for instance the commercial product sold under the name X-Tend 226® by the company ISP, octyl palmitate, isopropyl lanolate, diisopropyl sebacate, sold under the name Dub Dis by the company Stearinerie Dubois, triglycerides, including capric/caprylic acid triglycerides, and dicaprylyl carbonate sold under the name Cetiol CC by the company Cognis, oxyethylenated or oxypropylenated fatty esters and ethers; silicone oils (cyclomethicone and polydimethylsiloxanes, or PDMSs) or fluoro oils, polyalkylenes, and trialkyl trimellitates such as tridecyl trimellitate.

Waxy compounds that may be mentioned include carnauba wax, beeswax, hydrogenated castor oil, polyethylene waxes and polymethylene waxes, for instance the wax sold under the name Cirebelle 303 by the company Sasol.

Among the organic solvents that may be mentioned are lower alcohols and polyols. These polyols may be chosen from glycols and glycol ethers, for instance ethylene glycol, propylene glycol, butylene glycol, dipropylene glycol or diethylene glycol.

Hydrophilic thickeners that may be mentioned include carboxyvinyl polymers, such as Carbopols (Carbomers) and the Pemulens (acrylate/C10-C30 alkyl acrylate copolymer); polyacrylamides, for instance the crosslinked copolymers sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulphonic acid polymers and copolymers, optionally crosslinked and/or neutralized, for instance poly(2-acrylamido-2-methylpropanesulphonic acid) sold by the company Clariant under the trade name Hostacerin AMPS (CTFA name: ammonium polyacryloyldimethyl taurate or Simulgel 800 sold by the company SEPPIC(CTFA name: sodium polyacryolyldimethyl taurate/polysorbate 80/sorbitan oleate); copolymers of 2-acrylamido-2-methylpropanesulphonic acid and of hydroxyethyl acrylate, for instance Simulgel NS and Sepinov EMT 10 sold by the company SEPPIC; cellulose derivatives such as hydroxyethyl cellulose; polysaccharides and especially gums such as xanthan gum; water-soluble or water-dispersible silicone derivatives, for instance acrylic silicones, polyether silicones and cationic silicones, and mixtures thereof.

Lipophilic thickeners that may be mentioned include synthetic polymers, such as the poly(C10-C30 alkyl acrylates) sold under the names Intelimer IPA 13-1 and Intelimer IPA 13-6 by the company Landec, or modified clays, such as hectorite and its derivatives, for instance the products sold under the Bentone names.

Of course, a person skilled in the art will take care to select the aforementioned optional additional compound(s) and/or the amounts thereof such that the advantageous properties intrinsically associated with the compositions employed in accordance with the invention are not, or are not substantially, adversely affected by the envisaged addition(s).

The compositions employed for the photoprotection or care of the skin according to the invention, and the compositions comprising the compound A or the group of compounds A, can be prepared according to techniques well known to a person skilled in the art. They may in particular be in the form of a simple or complex emulsion (O/W, W/O, O/W/O or W/O/W) such as a cream, a milk or a cream-gel; in the form of an aqueous or oily gel; in the form of a lotion. They may optionally be packaged in aerosol form and may be in the form of a mousse or a spray.

The compositions employed according to the invention are preferably in the form of an oil-in-water or water-in-oil emulsion or also of an aqueous gel.

The emulsification processes that may be used are of the paddle or propeller, rotor-stator and HPH type.

It is also possible, via HHP (between 50 and 800 bar), to obtain stable dispersions with droplet sizes that may be as low as 100 nm.

The emulsions generally contain at least one emulsifier chosen from amphoteric, anionic, cationic or nonionic emulsifiers, used alone or as a mixture. The emulsifiers are appropriately chosen according to the emulsion to be obtained (W/O or O/W).

As emulsifying surfactants that may be used for the preparation of the W/O emulsions, examples that may be mentioned include alkyl esters or ethers of sorbitan, of glycerol or of sugars; silicone surfactants, for instance dimethicone copolyols, such as the mixture of cyclomethicone and of dimethicone copolyol, sold under the name DC 5225 C by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R by the company Goldschmidt, and the mixture of cetyldimethicone copolyol, of polyglyceryl isostearate (4 mol) and of hexyl laurate, sold under the name Abil WE 09 by the company Goldschmidt. One or more coemulsifiers may also be added thereto, which may be chosen advantageously from the group comprising polyol alkyl esters.

Polyol alkyl esters that may especially be mentioned include polyethylene glycol esters, for instance PEG-30 dipolyhydroxystearate, such as the product sold under the name Arlacel P135 by the company ICI.

Glycerol and/or sorbitan esters that may be mentioned include, for example, polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

For the O/W emulsions, examples of emulsifiers that may be mentioned include nonionic emulsifiers such as oxyalkylenated (more particularly polyoxyethylenated) esters of fatty acids and of glycerol; oxyalkylenated esters of fatty acids and of sorbitan; oxyalkylenated (oxyethylenated and/or oxypropylenated) esters of fatty acids, such as the PEG-100 stearate/glyceryl stearate mixture sold, for example, by ICI under the name Arlacel 165; oxyalkylenated (oxyethylenated and/or oxypropylenated) ethers of fatty alcohols; esters of sugars, such as sucrose stearate; or ethers of fatty alcohol and of sugar, in particular alkyl polyglucosides (APGs), such as decyl glucoside and lauryl glucoside, sold, for example, by the company Henkel under the respective names Plantaren 2000 and Plantaren 1200, cetostearyl glucoside, optionally as a mixture with cetostearyl alcohol, sold, for example, under the name Montanov 68 by the company SEPPIC, under the name Tegocare CG90 by the company Goldschmidt and under the name Emulgade KE3302 by the company Henkel, and also arachidyl glucoside, for example in the form of a mixture of arachidyl alcohol, behenyl alcohol and arachidyl glucoside, sold under the name Montanov 202 by the company SEPPIC. According to one particular embodiment of the invention, the mixture of the alkyl polyglucoside as defined above with the corresponding fatty alcohol can be in the form of a self-emulsifying composition, for example as described in document WO-A-92/06778.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The cosmetic compositions employed according to the invention may be used, for example, as care products and/or anti-sun protection products for the face and/or the body, of liquid to semi-liquid consistency, such as milks, more or less rich creams, cream-gels or pastes. They may optionally be packaged in aerosol form and may be in the form of a mousse or a spray.

The compositions according to the invention in the form of vaporizable fluid lotions in accordance with the invention are applied to the skin or the scalp in the form of fine particles by means of pressurization devices. The devices in accordance with the invention are well known to those skilled in the art and comprise non-aerosol pumps or "atomizers", aerosol containers comprising a propellant and also aerosol pumps using compressed air as propellant. These devices are described in U.S. Pat. Nos. 4,077,441 and 4,850,517 (which form an integral part of the content of the description).

The compositions conditioned in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

The compositions employed according to the invention may additionally also comprise additional cosmetic and dermatological active agents.

Mention may be made, among active agents, of:
vitamins (A, C, E, K, PP, etc.) and derivatives or precursors thereof, alone or as mixtures;
antiglycation agents;
calmatives;
NO-synthase inhibitors;
agents for stimulating the synthesis of dermal or epidermal macromolecules and/or for preventing their degradation;

agents for stimulating fibroblast proliferation;
agents for stimulating keratinocyte proliferation;
muscle relaxants;
tensioning agents;
matting agents;
keratolytic agents;
desquamating agents;
moisturizers, for instance polyols such as glycerol, butylene glycol or propylene glycol;
anti-inflammatory agents;
agents acting on the energy metabolism of cells,
insect repellents;
substance P or CGRP antagonists;
hair-loss counteractants and/or hair restorers;
anti-wrinkle agents.

Of course, a person skilled in the art will take care to select the aforementioned optional additional compound(s) and/or the amounts thereof such that the advantageous properties intrinsically associated with the compositions in accordance with the invention are not, or are not substantially, adversely affected by the envisaged addition(s).

A person skilled in the art will select the said active agent(s) as a function of the effect desired on the skin.

The composition may also comprise at least one ingredient such as fillers with a soft-focus effect or agents for promoting the natural coloration of the skin, intended to complement the biological effect of these active agents or to provide an immediate visual anti-ageing effect.

For caring for and/or making up greasy skin, a person skilled in the art will preferably choose at least one active agent chosen from desquamating agents, sebo-regulating agents or anti-seborrhoeic agents, and astringents.

The compositions employed according to the invention may also comprise at least one additional ingredient for complementing the biological effect of these active agents or for affording an immediate visual effect; mention may be made especially of matifying agents, soft-focus fillers, fluorescers, agents for promoting the naturally pinkish coloration of the skin, and abrasive fillers or exfoliants.

To complement and/or optimize the effects imparted by the cosmetic and/or dermatological active agents mentioned above on the keratin materials, it may be advantageous to incorporate into the compositions of the invention other additional ingredients.

In particular, these additional ingredients may impart an immediate visual effect that will be relayed by the biological effect of the active agents mentioned above. They may also, via a mechanical action (e.g.: abrasive fillers), amplify the effect of the biological active agents mentioned above.

Matting Agents

The term "matting agent" means agents intended to make the skin visibly more matt and less shiny.

The matting effect of the agent and/or composition containing it may especially be evaluated using a gonioreflectometer, by measuring the ratio R between the specular reflection and the scattered reflection. A value of R of less than or equal to 2 generally indicates a matting effect.

The matting agent may especially be chosen from a rice starch or a corn starch: INCI name: *Zea Mays* (Corn) Starch, such as, in particular, the product sold under the trade name Farmal CS 3650 Plus 036500 by National Starch, kaolinite, talc, a pumpkin seed extract, cellulose microbeads, plant fibres, synthetic fibres, in particular polyamide fibres, expanded acrylic copolymer microspheres, polyamide powders, silica powders, polytetrafluoroethylene powders, silicone resin powders, acrylic polymer powders, wax powders, polyethylene powders, powders of elastomeric crosslinked organopolysiloxane coated with silicone resin, talc/titanium dioxide/alumina/silica composite powders, amorphous mixed silicate powders, silicate particles and especially mixed silicate particles, and mixtures thereof.

Examples of matting agents that may especially be mentioned include:
rice or corn starch, in particular an aluminium starch octenyl succinate sold under the name Dry Floe by the company National Starch;
kaolinite;
silicas;
talc;
a pumpkin seed extract as sold under the name Curbilene® by the company Indena;
cellulose microbeads as described in patent application EP 1 562 562;
fibres, such as silk fibres, cotton fibres, wool fibres, flax fibres, cellulose fibres extracted especially from wood, from vegetables or from algae, polyamide (Nylon®) fibres, modified cellulose fibres, poly-p-phenylene terephthamide fibres, acrylic fibres, polyolefin fibres, glass fibres, silica fibres, aramid fibres, carbon fibres, Teflon® fibres, insoluble collagen fibres, polyester fibres, polyvinyl chloride or polyvinylidene chloride fibres, polyvinyl alcohol fibres, polyacrylonitrile fibres, chitosan fibres, polyurethane fibres, polyethylene phthalate fibres, fibres formed from a mixture of polymers, resorbable synthetic fibres, and mixtures thereof described in patent application EP 1 151 742;
expanded acrylic copolymer microspheres such as those sold by the company Expancel under the name Expancel 551®;
fillers with an optical effect as described in patent application FR 2 869 796, in particular:
polyamide (Nylon®) powders, for instance Nylon 12 particles of the Orgasol type from Arkema, with a mean size of 10 microns and a refractive index of 1.54,
silica powders, for instance Silica beads SB150 from Miyoshi with a mean size of 5 microns and a refractive index of 1.45,
polytetrafluoroethylene powders, for instance PTFE Ceridust 9205F from Clariant, with a mean size of 8 microns and a refractive index of 1.36,
silicone resin powders, for instance the silicone resin Tospearl 145A from GE Silicone with a mean size of 4.5 microns and a refractive index of 1.41,
acrylic copolymer powders, especially of polymethyl (meth)acrylate, for instance the PMMA particles Jurymer MBI from Nihon Junyoki, with a mean size of 8 microns and a refractive index of 1.49, or the Micropearl M100® and F 80 ED® particles from the company Matsumoto Yushi-Seiyaku,
wax powders, for instance the paraffin wax particles Microease 114S from Micropowders, with a mean size of 7 microns and a refractive index of 1.54,
polyethylene powders, especially comprising at least one ethylene/acrylic acid copolymer, and in particular consisting of ethylene/acrylic acid copolymers, for instance the Flobeads EA 209 particles from Sumitomo (with a mean size of 10 microns and a refractive index of 1.48),
elastomeric crosslinked organopolysiloxane powders coated with silicone resin, especially with silsesquioxane resin, as described, for example, in U.S. Pat. No. 5,538,793. Such elastomer powders are sold under the names KSP-100, KSP-101, KSP-102, KSP-103, KSP-104 and KSP-105 by the company Shin-Etsu, and talc/titanium dioxide/alumina/silica composite powders, such as those sold under the name Coverleaf® AR-80 by the company Catalyst & Chemicals, mixtures thereof, compounds that absorb and/or adsorb sebum as described in patent application FR 2 869 796. Mention may be made especially of:

silica powders, for instance the porous silica microspheres sold under the name Silica Beads SB-700 sold by the company Miyoshi, the products Sunsphere® H51, Sunsphere® H33 and Sunsphere® H53 sold by the company Asahi Glass; the polydimethylsiloxane-coated amorphous silica microspheres sold under the name SA Sunsphere® H-33 and SA Sunsphere® H-53 sold by the company Asahi Glass; amorphous mixed silicate powders, especially of aluminium and magnesium, for instance the product sold under the name Neusilin UFL2 by the company Sumitomo;

polyamide (Nylon®) powders, for instance Orgasol® 4000 sold by the company Arkema, and acrylic polymer powders, especially of polymethyl methacrylate, for instance Covabead® LH85 sold by the company Wackherr; of polymethyl methacrylate/ethylene glycol dimethacrylate, for instance Dow Corning 5640 Microsponge® Skin Oil Adsorber sold by the company Dow Corning, or Ganzpearl® GMP-0820 sold by the company Ganz Chemical; of polyallyl methacrylate/ethylene glycol dimethacrylate, for instance Poly-Pore® L200 or Poly-Pore® E200 sold by the company Amcol; of ethylene glycol dimethacrylate/lauryl methacrylate copolymer, for instance Polytrap® 6603 sold by the company Dow Corning;

silicate particles, such as alumina silicate;

mixed silicate particles, such as:

magnesium aluminium silicate particles, such as saponite or hydrated magnesium aluminium silicate with a sodium sulphate sold under the trade name Sumecton® by the company Kunimine;

the magnesium silicate, hydroxyethylcellulose, black cumin oil, marrow oil and phospholipids complex or Matipure® from Lucas Meyer, and mixtures thereof.

Preferred matting agents that may be used according to the invention include a pumpkin seed extract, a rice or corn starch, kaolinite, silicas, talc, polyamide powders, polyethylene powders, acrylic copolymer powders, expanded acrylic copolymer microspheres, silicone resin microbeads and mixed silicate particles, and mixtures thereof.

Fillers with a Soft-focus Effect

These fillers can be any material capable of modifying wrinkles via its intrinsic physical properties and of concealing them. These fillers may especially modify wrinkles via a tensioning effect, a covering effect or a soft-focus effect.

The following compounds may be given as examples of fillers:

porous silica microparticles, for instance the Silica Beads® SB 150 and SB 700 from Miyoshi with a mean size of 5 µm; the series H Sunspheres® from Asahi Glass, for instance Sunspheres H33, H51 with respective sizes of 3.5 and 5 µm; hollow hemispherical silicone resin particles such as NLK 500®, NLK 506® and NLK 510® from Takemoto Oil and Fat, especially described in EP-A-1 579 849;

silicone resin powders, for instance the silicone resin Tospearl® 145 A from GE Silicone, with a mean size of 4.5 µm;

acrylic copolymer powders, especially of polymethyl (meth)acrylate, for instance the PMMA particles Jurimer MBI® from Nihon Junyoki, with a mean size of 8 µm, the hollow PMMA spheres sold under the name Covabead® LH 85 by the company Wackherr, and vinylidene/acrylonitrile/methylene methacrylate expanded microspheres sold under the name Expancel®;

wax powders, for instance the paraffin wax particles MicroEase® 114S from MicroPowders, with a mean size of 7 µm;

polyethylene powders, especially comprising at least one ethylene/acrylic acid copolymer, for instance the Flobeads® EA 209 E particles from Sumitomo, with a mean size of 10 µm;

crosslinked elastomeric organopolysiloxane powders coated with silicone resin and especially with silsesquioxane resin, under the names KSP-100®, KSP-1010, KSP-102®, KSP-103®, KSP-104® and KSP-105® by the company Shin-Etsu;

talc/titanium dioxide/alumina/silica composite powders, for instance those sold under the name Coverleaf AR-80® by the company Catalyst & Chemicals;

talc, mica, kaolin, lauryl glycine, starch powders crosslinked with octenylsuccinic anhydride, boron nitride, polytetrafluoroethylene powders, precipitated calcium carbonate, magnesium carbonate, basic magnesium carbonate, barium sulphate, hydroxyapatite, calcium silicate, cerium dioxide and glass or ceramic microcapsules;

hydrophilic or hydrophobic, synthetic or natural, mineral or organic fibres such as silk fibres, cotton fibres, wool fibres, flax fibres, cellulose fibres extracted especially from wood, vegetables or algae, polyamide (Nylon®) fibres, modified cellulose fibres, poly-p-phenylene terephthalamide fibres, acrylic fibres, polyolefin fibres, glass fibres, silica fibres, aramid fibres, carbon fibres, polytetrafluoroethylene (Teflon®) fibres, insoluble collagen fibres, polyester fibres, polyvinyl chloride fibres, polyvinylidene chloride fibres, polyvinyl alcohol fibres, polyacrylonitrile fibres, chitosan fibres, polyurethane fibres, polyethylene phthalate fibres, fibres formed from a mixture of polymers, resorbable synthetic fibres, and mixtures thereof described in patent application EP 1 151 742;

spherical elastomeric crosslinked silicones, for instance Trefil E-505C® or E-506C® from Dow Corning;

abrasive fillers, which, via a mechanical effect, smooth out the skin microrelief, such as abrasive silica, for instance Abrasif SP® from Semanez, or nut or shell powders (for example of apricot or walnut, from Cosmetochem).

The fillers with an effect on the signs of ageing are especially chosen from porous silica microparticles, hollow hemispherical silicone particles, silicone resin powders, acrylic copolymer powders, polyethylene powders, crosslinked elastomeric organopolysiloxane powders coated with silicone resin, talc/titanium dioxide/alumina/silica composite powders, precipitated calcium carbonate, magnesium carbonate, magnesium hydrogen carbonate, barium sulphate, hydroxyapatite, calcium silicate, cerium dioxide, glass or ceramic microcapsules, and silk fibres or cotton fibres, and mixtures thereof.

The filler may be a soft-focus filler.

The term "soft-focus" filler means a filler which in addition gives the complexion transparency and a hazy effect. Preferably, the soft-focus fillers have a mean particle size of less than or equal to 15 microns. These particles may be in any form and in particular may be spherical or non-spherical. These fillers are more preferably non-spherical.

The soft-focus fillers may be chosen from silica and silicate powders, especially alumina powder, powders of polymethyl methacrylate (PMMA) type, talc, silica/TiO2 or silica/zinc oxide composites, polyethylene powders, starch powders, polyamide powders, styrene/acrylic copolymer powders and silicone elastomers, and mixtures thereof.

Mention may be made in particular of talc with a number-average size of less than or equal to 3 microns, for example talc with a number-average size of 1.8 microns and especially that sold under the trade name Talc P3® by the company Nippon Talc, Nylon® 12 powder, especially that sold under the name Orgasol 2002 Extra D Nat Cos® by the company Atochem, silica particles 1% to 2% surface-treated with a mineral wax (INCI name: hydrated silica (and) paraffin) such as those sold by the company Degussa, amorphous silica microspheres, such as those sold under the name Sunsphere, for example of reference H-53® by the company Asahi Glass, and silica microbeads such as those sold under the name SB-700® or SB-150® by the company Miyoshi, this list not being limiting.

The concentration of these fillers with an effect on the signs of ageing in the compositions according to the invention may be between 0.1% and 40%, or even between 0.1% and 20% by weight, relative to the total weight of the composition.

Agents for Promoting the Naturally Pinkish Coloration of the Skin

The compositions used according to the invention may also comprise an agent for promoting the naturally pinkish coloration of the skin. Mention may be made especially of:
  a self-tanning agent, i.e. an agent which, when applied to the skin, especially to the face, can produce a tan effect that is more or less similar in appearance to that which may result from prolonged exposure to the sun (natural tan) or under a UV lamp;
  an additional colouring agent, i.e. any compound that has particular affinity for the skin, which allows it to give the skin a lasting, non-covering coloration (i.e. that does not have a tendency to opacify the skin) and that is not removed either with water or using a solvent, and that withstands both rubbing and washing with a solution containing surfactants. Such a lasting coloration is thus distinguished from the superficial and transient coloration provided, for example, by a makeup pigment; and mixtures thereof.

Examples of self-tanning agents that may especially be mentioned include:
dihydroxyacetone (DHA) (used as a supplement to a compound C for photoprotection (or screening agent) or care of the skin),
  erythrulose, and
  the combination of a catalytic system formed from:
  manganese and/or zinc salts and oxides, and
  alkali metal and/or alkaline-earth metal hydrogen carbonates.

The self-tanning agents are generally chosen from monocarbonyl or polycarbonyl compounds, for instance isatin, alloxan, ninhydrin, glyceraldehyde, mesotartaric aldehyde, glutaraldehyde, erythrulose, pyrazolin-4,5-dione derivatives as described in patent application FR 2 466 492 and WO 97/35842, dihydroxyacetone (DHA) and 4,4-dihydroxypyrazolin-5-one derivatives as described in patent application EP 903 342. DHA will preferably be used.

DHA may be used in free and/or encapsulated form, for example in lipid vesicles such as liposomes, described especially in patent application WO 97/25970.

In general, the self-tanning agent is present in an amount ranging from 0.01% to 20% by weight and preferably in an amount of between 0.1% and 10% of the total weight of the composition.

Other dyes that allow modification of the colour produced by the self-tanning agent may also be used.

These dyes may be chosen from synthetic or natural direct dyes.

These dyes may be chosen, for example, from red or orange dyes of the fluorane type such as those described in patent application FR 2 840 806. Mention may be made, for example, of the following dyes:
  tetrabromofluorescein or eosin known under the CTFA name: CI-45380 or Red 21
  phloxin B known under the CTFA name: CI-45410 or Red 27
  diiodofluorescein known under the CTFA name: CI-45425 or Orange 10;
  dibromofluorescein known under the CTFA name: CI-45370 or Orange 5;
  the sodium salt of tetrabromofluorescein known under the CTFA name: CI-45380 (Na salt) or Red 22;
  the sodium salt of phloxin B known under the CTFA name: CI-45410 (Na salt) or Red 28;
  the sodium salt of diiodofluorescein known under the CTFA name: CI-45425 (Na salt) or Orange 11;
  erythrosine known under the CTFA name: CI-45430 or Acid Red 51;
  phloxin known under the CTFA name: CI-45405 or Acid Red 98;

These dyes can also be chosen from anthraquinones, caramel, carmine, carbon black, azulene blues, methoxsalen, trioxsalen, guaiazulene, chamazulene, rose bengal, eosin 10B, cyanosine or daphinine.

These dyes may also be chosen from indole derivatives, for instance the monohydroxyindoles as described in patent FR 2 651 126 (i.e.: 4-, 5-, 6- or 7-hydroxyindole) or the dihydroxyindoles as described in patent EP-B-0 425 324 (i.e.: 5,6-dihydroxyindole, 2-methyl-5,6-dihydroxyindole, 3-methyl-5,6-dihydroxyindole or 2,3-dimethyl-5,6-dihydroxyindole).

Abrasive Fillers or Exfoliants

As exfoliants that may be used in rinse-out compositions according to the invention, examples that may be mentioned include exfoliant or scrubbing particles of mineral, plant or organic origin. Thus, use may be made, for example, of polyethylene beads or powder, nylon powder, polyvinyl chloride powder, pumice, ground materials derived from apricot kernels or walnut shells, sawdust, glass beads, alumina and their mixtures. Mention may also be made of Exfogreen® from Solabia (bamboo extract), extracts of strawberry achenes (strawberry achenes from Greentech), peach kernel powder or apricot kernel powder and, finally, mention may be made, in the field of plant powders with an abrasive effect, of cranberry seed powder.

Mention will be made, as preferred abrasive fillers or exfoliants according to the invention, of peach kernel powder, apricot kernel powder, cranberry seed powder, extracts of strawberry achenes or bamboo extracts.

The invention also relates to a cosmetic assembly or kit comprising at least:
  a first composition comprising, in a physiologically acceptable medium, at least one compound or group of compounds A as described above;
  a second composition comprising, in a physiologically acceptable medium, at least one screening agent C as described above.

The assembly according to the invention can thus be composed of a two-compartment system. It can also correspond to an assembly comprising the first composition in a first formulation form (for example, a cream comprising the compound or group of compounds A) and the second composition in a second formulation form.

The examples below are given as non-limiting illustrations of the field of the invention.

EXAMPLES

Formulations Comprising an Alkoxysilane Having a Free Amine Functional Group:

| Ingredients | Ex. a | Ex. b | Ex. c | Ex. d |
|---|---|---|---|---|
| APTES | 3.33 | 5 | 6.7 | 10 |
| Lactic acid | 0.5 | 0.75 | 1 | 1.5 |
| Preservative | 0.3 | 0.3 | 0.3 | 0.3 |
| Water | qs | qs | qs | qs |

Examples of Compositions with UV Screening Agents

| Ingredients | Ex. 1 | Ex. 2 |
|---|---|---|
| Phenylbenzimidazole Sulfonic Acid (Eusolex 232) | 4 | 6 |
| Terephthalylidene Dicamphor Sulfonic Acid (Mexoryl SX (Comprising 33% AM)) | 4 MA (*) | 6 MA (*) |
| TRIETHANOLAMINE | 5.13 | 7.7 |
| PRESERVATIVE | 0.3 | 0.3 |
| WATER | qs | qs |

(*) Active Material

Demonstration of the Improvement in the Screening and Persistence Towards Water Properties Principle of the Assay:

The screening effectiveness and the persistence towards water of a solution of UV screening agents, applied to a condensed deposited layer of APTES, in comparison with a solution deposited on bare skin, are evaluated and compared at different concentrations. The UV screening agents tested are Phenylbenzimidazole Sulfonic Acid and Terephthalylidene Dicamphor Sulfonic Acid.

The studies were carried out on 5 volunteers of phototype I, II or III. The studies targeted exclusively at determining the screening effectiveness took place over 2 consecutive days, when 3 days were necessary for measurements of persistence towards water. On the first day, the screening formulation is applied at 2 mg per cm² on bare skin or on a condensed deposited layer of APTES. The volunteers are subsequently exposed to ultraviolet radiation. Erythema is read and the SPF is defined 24 h later. In the case of a test of persistence towards water, the same solutions or pairs of solutions are applied on the second day. The volunteers are immersed in 2 consecutive baths of water, each of 20 minutes, Wore being again exposed to UV radiation. The post-bath SPF is determined during the third test day. The water resistance (WR) is defined as:

$$WR(\%) = \frac{(SPF_{post\text{-}bath} - 1)}{(SPF_{pre\text{-}bath} - 1)} \times 100$$

The formulae 1 and 2 tested are stable after 2 months at ambient temperature and exhibit very good sensory qualities after application to the skin.

The formulae are tested with successive application of the APTES solution and then of the screening solution. The various conditions tested are as follows:

Conditions I and II were tested for SPF and water resistance.

Conditions I, II, III, IV, V and VI were tested for SPF.

I=> Example 2
II=> Example 2+Example b (50/50)
III=> Example 2+Example d (50/50)
IV=> Example 1
V=> Example 1+Example a (50/50)
VI=> Example 1+Example c (50/50)

The SPF values of the 8% and 12% solutions of UV screening agents are measured, which measurements are taken after spreading over bare skin or over deposited layers more or less concentrated in APTES.

The APTES/UV screening agents ratio corresponds to the ratio between the weights of APTES and UV screening agents (Mexoryl SX+Eusolex 232) deposited on the skin.

The water resistance of the 12% solution of UV screening agents was also evaluated in vivo, with and without APTES. The comparative water resistance data in the following table.

| Formula | Water resistance (%) in vivo |
|---|---|
| EXAMPLE 2 | 1.9 |
| Example 2 and Example b | 26.1 |

The APTES layer makes it possible to significantly increase the resistance to water of the UV screening agents, which are nevertheless water-soluble, of Example 2.

The 8%, like 12%, screening solutions of UV screening agents exhibit a greater SPF in vivo if they are spread over a deposited layer of APTES.

Figure 1:
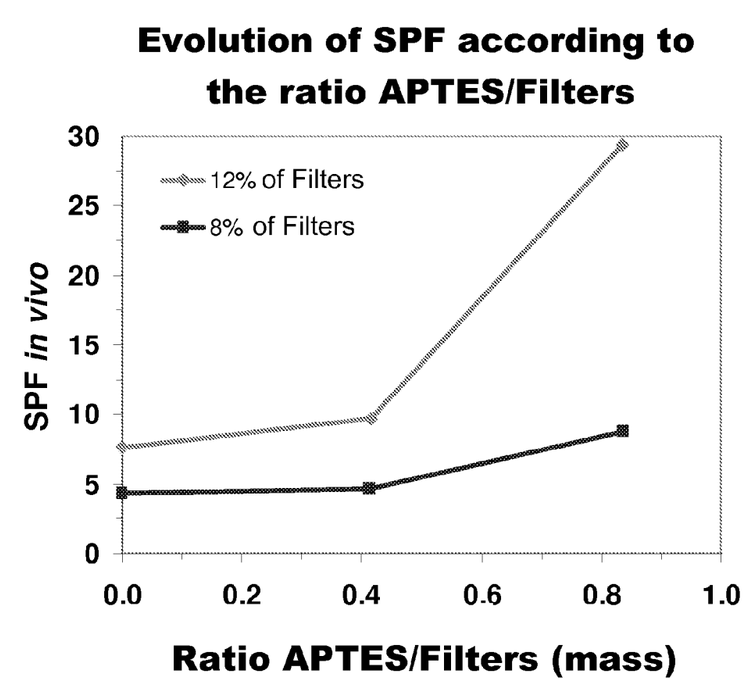

In this study, a dose effect of the APTES was demonstrated: the SPF increases in proportion as the amount of APTES spread beforehand over the skin increases (see FIG. 1).

The invention claimed is:

1. Method for the cosmetic treatment of the skin, comprising the application, to the skin:

of a compound or group of compounds A capable of condensing in situ and exhibiting at least one reactive functional group FA which is free after condensation, wherein the reactive functional group is an amine and wherein the compound A corresponds to the formula:

in which:
R$_4$ represents a halogen or an OR' or R'$_1$ group;
R$_5$ represents a halogen or an OR' or R'$_2$ group;
R$_6$ represents a halogen or an OR''' or R'$_3$ group;
and R$_1$, R$_2$, R$_3$, R', R'', R''', R'$_1$, R'$_2$ and R'$_3$ represent, independently of one another, a linear or branched and saturated or unsaturated hydrocarbon group carrying additional an amine group, it being possible in addition for R$_1$, R$_2$, R', R'' and R''' to in addition denote hydrogen; and at least two of the groups R$_4$, R$_5$ and R$_6$ being different from the groups R'$_1$, R'$_2$ and R'$_3$; and of a screening agent C which screens out UV radiation, comprising a reactive functional group FC capable of forming a covalent bond or a physical (ionic, hydrogen) bond by reaction with the reactive functional group FA.

2. Method according to claim 1, in which the reactive functional group is a primary amine.

3. Method according to claim 1, in which A is γ aminopropyltriethoxysilane (APTES).

4. Method according to claim 1, where the screening agent C is chosen from cinnamic derivatives; anthranilates; salicylic derivatives; dibenzoylmethane derivatives; camphor derivatives; hydroxyphenyl benzophenone derivatives; β,β-diphenylacrylate derivatives; triazine derivatives; benzotriazole derivatives; benzalmalonate derivatives; benzimidazole derivatives; imidazolines; bis-benzazolyl derivatives; p-aminobenzoic acid (PABA) derivatives; methylenebis(hydroxyphenylbenzotriazole) derivatives; benzoxazole derivatives; screening polymers and screening silicones; α-alkylstyrene-based dimers; 4,4-diarylbutadienes; merocyanin derivatives; and mixtures thereof.

5. Method according to claim 1, where the screening agent C is chosen from organic UV screening agents.

6. Method according to claim 5, where the screening agent C is chosen from Phenylbenzimidazole Sulfonic Acid, Terephthalylidene Dicamphor Sulfonic Acid, Disodium Phenyl Dibenzimidazole Tetrasulfonate or their mixtures.

7. Method according to claim 1, comprising a sequential application of the compounds with:

in a first step, the application of the compound or of the group of compounds A;

in a second step, the application of the screening agent C.

8. Method according to claim 1, where the compounds A and C are mixed before application to the skin (extemporaneous mixing); it being possible for the said mixing to be carried out before application or during the application to the skin (mixing directly on the region of the skin to be treated).

9. Cosmetic assembly comprising at least:

a first composition comprising, in a physiologically acceptable medium, at least one compound or group of compounds A as defined in claim 1;

a second composition comprising, in a physiologically acceptable medium, at least one screening agent C which screens out UV radiation, comprising a reactive functional group FC capable of forming a covalent bond or a physical (ionic, hydrogen) bond by reaction with the reactive functional group FA.

10. Method according to claim 4, in which the reactive functional group is a primary amine.

11. Method according to claim 4, in which A is γ aminopropyltriethoxysilane (APTES).

12. Method according to claim 5, in which A is γ aminopropyltriethoxysilane (APTES).

13. Method according to claim 6, in which A is γ aminopropyltriethoxysilane (APTES).

* * * * *